(12) United States Patent
Ricci et al.

(10) Patent No.: US 6,770,695 B2
(45) Date of Patent: Aug. 3, 2004

US006770695B2

(54) TIME RELEASE CALCIUM SULFATE MATRIX FOR BONE AUGMENTATION

(76) Inventors: John L. Ricci, 46 Verdun Pl., Middleton, NJ (US) 07748; Harold Alexander, 47 Elmwood Pl., Short Hills, NJ (US) 07078; Bruce Hollander, 312 S. Military Trail, Boca Raton, FL (US) 33442

(*) Notice: Subject to any disclaimer, the term of this patent is extended or adjusted under 35 U.S.C. 154(b) by 166 days.

(21) Appl. No.: 09/918,445

(22) Filed: Aug. 1, 2001

(65) Prior Publication Data
US 2002/0016636 A1 Feb. 7, 2002

Related U.S. Application Data
(60) Provisional application No. 60/223,624, filed on Aug. 7, 2000.

(51) Int. Cl.[7] ............................. C08K 3/30; A61K 6/08; A61K 9/14; A61K 27/14
(52) U.S. Cl. ...................... 524/423; 523/109; 523/113; 523/114; 523/115; 523/205; 523/351; 424/426; 424/486; 424/497
(58) Field of Search ...................... 524/423; 523/109, 523/113, 114, 115, 205, 351; 424/426, 486, 497

(56) References Cited
U.S. PATENT DOCUMENTS

| | | | | |
|---|---|---|---|---|
| 5,085,861 A | * | 2/1992 | Gerhart et al. | |
| 5,681,873 A | * | 10/1997 | Norton et al. | |
| 5,747,390 A | * | 5/1998 | Cooper et al. | |
| 6,048,521 A | * | 4/2000 | Kohn et al. | |
| 6,224,635 B1 | * | 5/2001 | Ricci et al. | |
| 2002/0110541 A1 | * | 8/2002 | Petersen | |

* cited by examiner

*Primary Examiner*—Tae H. Yoon
(74) *Attorney, Agent, or Firm*—M. K. Silverman; Yi Li

(57) ABSTRACT

An implant composition having controlled resorption rate in vivo for stimulating bone growth, a method of making the implant composition, and a kit of implant materials are disclosed. The implant composition includes a calcium sulfate compound, polymer containing particles, and a setting agent for setting the calcium sulfate compound and the polymer containing particles into a heterogeneous solid composition. Upon setting, the calcium sulfate compound forms a matrix and the polymer containing particles settled within the matrix. The resorption rate of the implant composition in vivo can be controlled of between eight and twenty-four weeks, which substantially matches the rate of bone growth. The implant composition of the present invention can be used for the repair, augmentation, and other treatment of bone.

69 Claims, 6 Drawing Sheets

TIME RELEASE CALCIUM SULFATE MATRIX FOR BONE AUGMENTATION

REFERENCE TO RELATED APPLICATION

This application corresponds in part to the subject matter to that of Provisional Application serial No. 60/223,624, filed Aug. 7, 2000, which is herein incorporated by reference in its entirety.

BACKGROUND OF THE INVENTION

The repair of bone defects and augmentation of existing bone often require the use of permanent bio-resorbable materials. Such materials may include autogenous bone graft, allogeneic graft, allogeneic bone graft, or alloplastic materials inclusive of various calcium phosphate ceramics, calcium phosphate cements, calcium sulfate materials, bioglass materials, and composites or other combinations thereof. Calcium sulfate, which is a form of plaster of paris, is a fully bioresorbable material which, for sometime, has been commonly used in cement and pellet form to repair bone defects.

When calcium sulfate is used as a cement to fill a bone void, fracture, or other defect, this material dissolves at a rapid rate, i.e., approximately one millimeter per week from the exterior of the cement towards the center thereof. Research of the present inventors has shown that this material causes precipitation of calcium phosphate deposits as it is resorbed at the surgical site. These precipitates, it has been shown, stimulate and direct the formation of new bone. On the other hand, it is important for purposes of optimal result that calcium sulfate, calcium phosphate, or any other bone repair material stay at the surgical site for a considerable period of time in order to inhibit soft tissue filling of the defect and to stimulate bone repair. However, currently used calcium sulfate materials are resorbed by human bone within two to seven weeks, depending upon the calcium sulfate form and the particular surgical site, which cannot be retained at the site for longer periods. As noted, such material is resorbed faster than it can be replaced by new bone thereby reducing its value to both patient and practitioner.

As such, the principal concern and difficulty expressed by practitioners (such as orthopedics or maxiofacial surgeons) are that calcium sulfate materials bio-resorb or dissolve too rapidly at a surgical or a recipient site, and, thereby, outpace the formation of new bone in human patients. Therefore, a need arises for improved calcium sulfate based compositions which can resorb at the recipient site in a rate desirably matching the rate bone growth.

SUMMARY OF THE INVENTION

The present invention relates to an implant composition having controlled resorption rate in vivo for stimulating bone growth, a method of making the implant composition, and a kit of implant materials.

In one aspect of the present invention, an implant composition having controlled resorption rate comprises a calcium sulfate compound, polymer containing particles, and a setting agent for setting the calcium sulfate compound and the polymer containing particles into a heterogeneous solid composition. Upon setting, the calcium sulfate compound forms a matrix and the polymer containing particles settled within the matrix.

In another aspect, the present invention comprises a method of using implant materials to make the inventive implant composition for bone augmentation and bone defect reparation. The method comprises the steps of: (a) mixing a calcium sulfate compound and polymer containing particles with a setting agent into a mixture, (b) applying the mixture, either by filling in a recipient site with the mixture, or by coating the mixture on a surface of a surgical implant prior to introducing the surgical implant into the recipient site, and (c) setting the mixture into a heterogeneous solid composition.

In a further aspect, the present invention relates to a kit of implant materials for bone augmentation and bone defect reparation. The kit comprises (a) dry powder of a calcium sulfate compound, and (b) polymer containing particles. The kit can further comprise a setting agent packed in a container, and instructions on how to use the kit for preparing the implant composition.

It is accordingly an object of the present invention to provide an implant composition for the repair and augmentation of bone defects.

It is another object of the invention to provide an implant composition having controllable resorption rate in vivo, wherein the rate of resorption can be substantially matched to the rate of bone growth in a specific medical or dental application.

It is a further object of the invention to provide implant materials and a method for making the implant composition.

The above and yet other objects and advantages of the present invention will become apparent from the hereinafter set forth Brief Description of the Drawings and Detailed Description of the Invention.

DETAILED DESCRIPTION OF THE INVENTION

Figure 1:
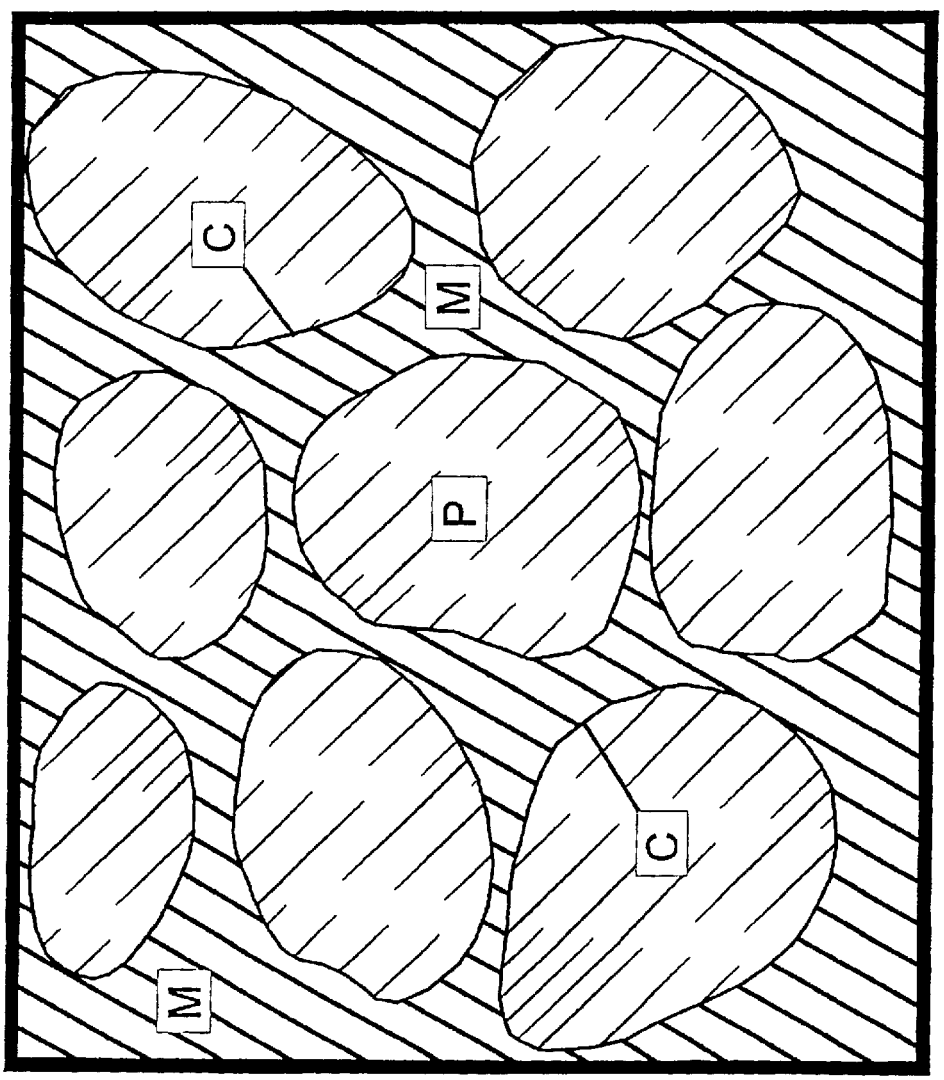
FIG. 1 is a schematic view of an implant composition of one embodiment of the present invention immediately after introduction into a recipient site, showing the heterogeneous solid implant composition.

In one aspect of the present invention, an implant composition having controlled resorption rate comprises a calcium sulfate compound, polymer containing particles, and a setting agent for setting the calcium sulfate compound and the polymer containing particles into a heterogeneous solid composition. Upon setting, the calcium sulfate compound forms a matrix (M) and the polymer containing particles (P) settled within the matrix. FIG. 1 shows a cross-sectional schematic view of the heterogeneous solid implant composition before resorption occurs.

In another aspect, the present invention comprises a method of using implant materials to make the inventive implant composition for bone augmentation and bone defect reparation. The method comprises the steps of: (a) mixing a calcium sulfate compound and polymer containing particles with a setting agent into a mixture, (b) filing a recipient site with the mixture, and (c) setting the mixture into a heterogeneous solid composition.

The calcium sulfate compound is dry powder of calcium sulfate hemihydrate. Suitable setting agents include water, alkaline metal salt solutions such as a saline solution, and an accelerant aqueous solution containing potassium salt. The setting agents set the implant materials into a heterogeneous solid composition, or a multiphasic cement with different speeds. The speed of setting can be controlled from seven minutes to one hour, depending on the setting agent used as well as desired surgical application. Among various setting agents, potassium salt solutions result in the fastest setting. For the purpose of the present invention, an aqueous solution containing potassium or sodium ions are preferably used. Most preferably, an aqueous solution containing potassium ions can be used. Suitable examples of potassium salts include potassium sulfate, potassium phosphate, and potassium fluoride. The concentration of potassium ion controls the speed of setting, the higher it is the faster the setting process. Preferably, the concentration of the potassium ions is in a range from about 0.01 molar to about 0.5 molar.

The polymer containing particles (P) comprises a calcium sulfate compound, and at least one resorbable polymer. The calcium sulfate compound in the polymer containing particles can be calcium sulfate dihydrate, also called preset calcium sulfate, or calcium sulfate hemihydrate, also called unset calcium sulfate, or a mixture thereof. In one embodiment, the calcium sulfate compound is mixed with a resorbable polymer to form the particles. The amount of resorbable polymer used in the particles controls resorption rate of the implant composition when it is implanted in a recipient site. In an alternative embodiment, the calcium sulfate compound of the particles is encapsulated in a coating (C) of a resorbable polymer, as shown in FIG. 1. In this case, thickness of the resorbable polymer coating controls resorption rate of the implant composition in a recipient site. The thickness of the resorbable polymer coating is from about 2 $\mu$m to about 50 $\mu$m. For polymers that are only expected to last for a short time, a thin layer can be applied. For fast-resorbing coatings, or coatings expected to last for a long time, a thick coating can be applied. Furthermore, the resorbable polymer coating is not required to be a complete encapsulation. It has been observed that small local incomplete coatings, or coatings with defects (accidentally or intentionally), function as initial resorption sites of the polymer containing particles. An analogous situation can be found in time release medicine. It is known that medical pills with small controlled defects (drilled or molded) in polymer coatings are sometimes used to control drug release rates. A broad range of particle sizes can be used in the implant composition. The particle size can be determined depended on a particular application, and recipient site. For example, small particles are more suitable for dental fillings. On the other hand, larger pallets are more suitable for repairing bone fracture. Preferably, the particle size is more than 20 $\mu$m in diameter since when the particles are smaller than 20 $\mu$m, they may cause a negative foreign body response due to activation of macrophages.

In an additional embodiment, the particles can be made having combined characteristics of the two types of particles described above. Herein, the particles can include mixed calcium sulfate compound and a resorbable polymer, which are, additionally, encapsulated with a resorbable polymer coating.

In a further embodiment, the implant composition comprises two different types of polymer containing particles that have different rates of resorption. Such particles can, for example, be particles coated with different polymers, combinations of coated and mixed polymers, or particles with coating of different thickness, a typical range being 0.5 to 100 micrometers.

A wide variety of resorbable polymers can be used for the implant composition of the present invention. Suitable resorbable polymers include aliphatic polyesters of alpha-hydroxy acid derivatives, such as polyactides, polyglycolides, polydioxanone, and poly $\epsilon$-caprolactone; hydrophobic polymers, such as carnuba waxes and their derivatives; water soluble polymers, such as poly (desaminotyrosyl-tyrosine ethyl ester carbonate), hereinafter poly (DTE carbonate) and their derivatives; and therapeutic polymers, such as those containing salicylate. A specific type of resorbable polymer can be selected depending on the purpose of applications, expected bone growth speed of a particular surgical site, and environment or condition of a recipient site. For the purpose of the present invention, polyactides, polyglycolides and poly (DTE carbonate) are used preferably. It is known that polyactides, including D and L isomers, and DL copolymers of polylactic acid, have a long time history in their use as biomedical devices. These polymers are readily available commercially. The polyglycolides and poly (DTE carbonate) have also been used for bone reparation.

In general, resorbable polymers resorb slower in vivo than calcium sulfate compounds. Therefore, the amount of resorbable polymer used in the particles, mixed or coated, controls resorption rate of the implant composition when it is implanted in a recipient site. The polymer containing particles can comprise about 0.1% to about 50% (w/w) of a resorbable polymer, with about 1.5% defining the best mode. When the amount of a resorbable polymer is too high, it may cause a negative body, that is, immune response. When used as a coating only, the above (w/w) range is about 0.1% to about 22%. The rate of resorption of the implant composition can be controlled of between three (3) and twenty eight (28) weeks, depending on the types and amount of polymers used.

In an additional embodiment, the present invention relates to a method of preparing the polymer containing particles. The polymer containing particles can be prepared by two methods: (1) a surface coating process, and (2) bulk mixing of polymer and calcium sulfate. In the surface coating process, preformed calcium sulfate particles are mixed with a polymer solution. The polymer solution forms a liquid coating on the calcium sulfate particles, and is allowed to dry and to form a polymer surface coating on the particles. The coating thickness and amount of penetration into the calcium sulfate depend on the concentration of polymer in the solution, and viscosity of the solution. Examples of suitable organic solvent can be used to dissolve the polymer and make the polymer solution include acetone and chloroform. In the bulk mixing method, a fine granular form of a polymer is mixed with a granular form of calcium sulfate. The mixture is then pressed or rolled into larger particles.

Figure 2:
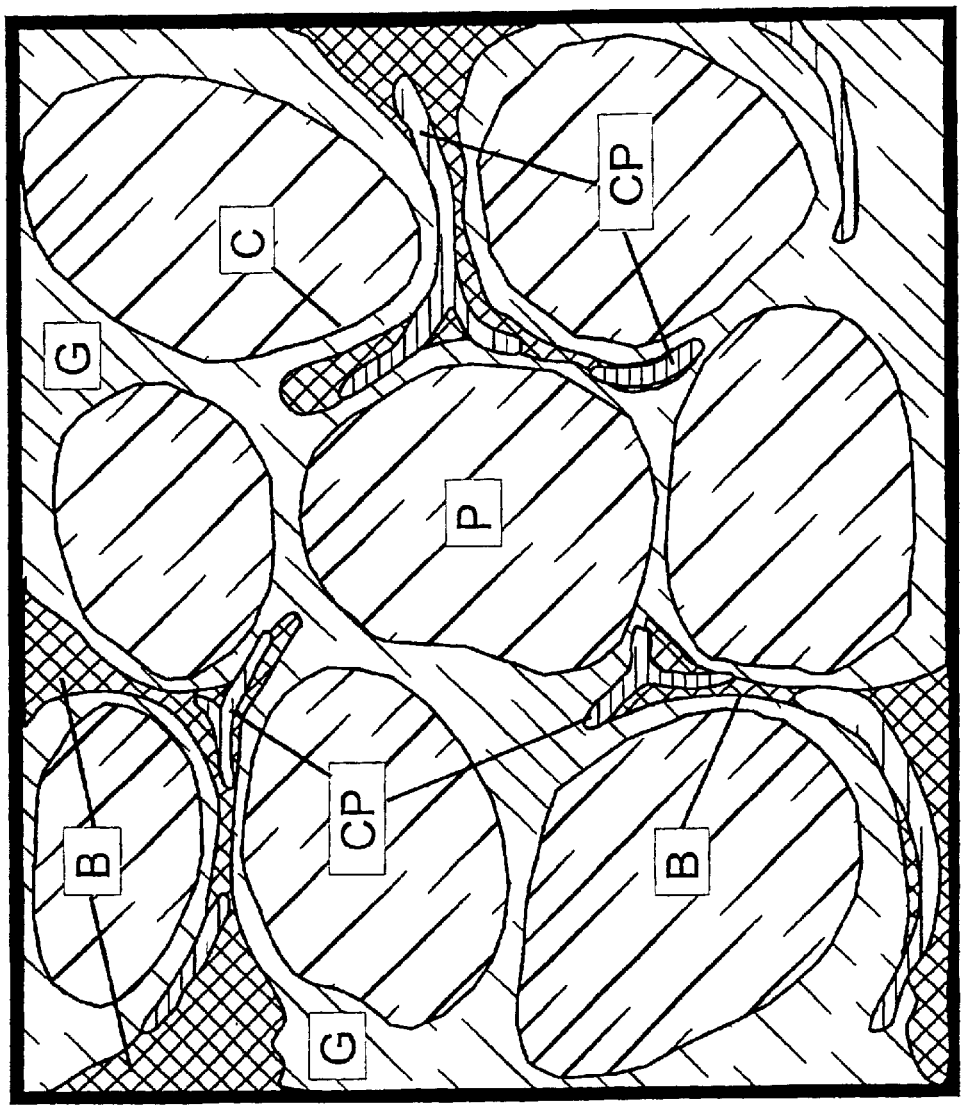
FIG. 2 is a view, sequential to that of FIG. 1, showing a first phase of bioresorption of the implant composition at the recipient site.

FIG. 1 to FIG. 4 illustrate the resorption process of the implant composition of the present invention, and the mechanism of controlled resorption rate for a proper stimulation of bone growth. FIG. 1 shows the structure of the heterogeneous solid implant composition after the mixture of calcium sulfate compound, polymer encapsulated particles, and the setting agent is being applied in a recipient site, and set into a heterogeneous solid composition. FIG. 2 shows the first phase of bioresorption of the implant composition. The calcium sulfate compound in the matrix resorbs first, that is, the first two to four weeks after implantation, thereby forming a porous system which will fill with granulation tissue (G) during said timeframe. The process of resorbing calcium sulfate forms deposits of calcium phosphate (CP) which has function to encourage early bone ingrowth (B).

Figure 3:
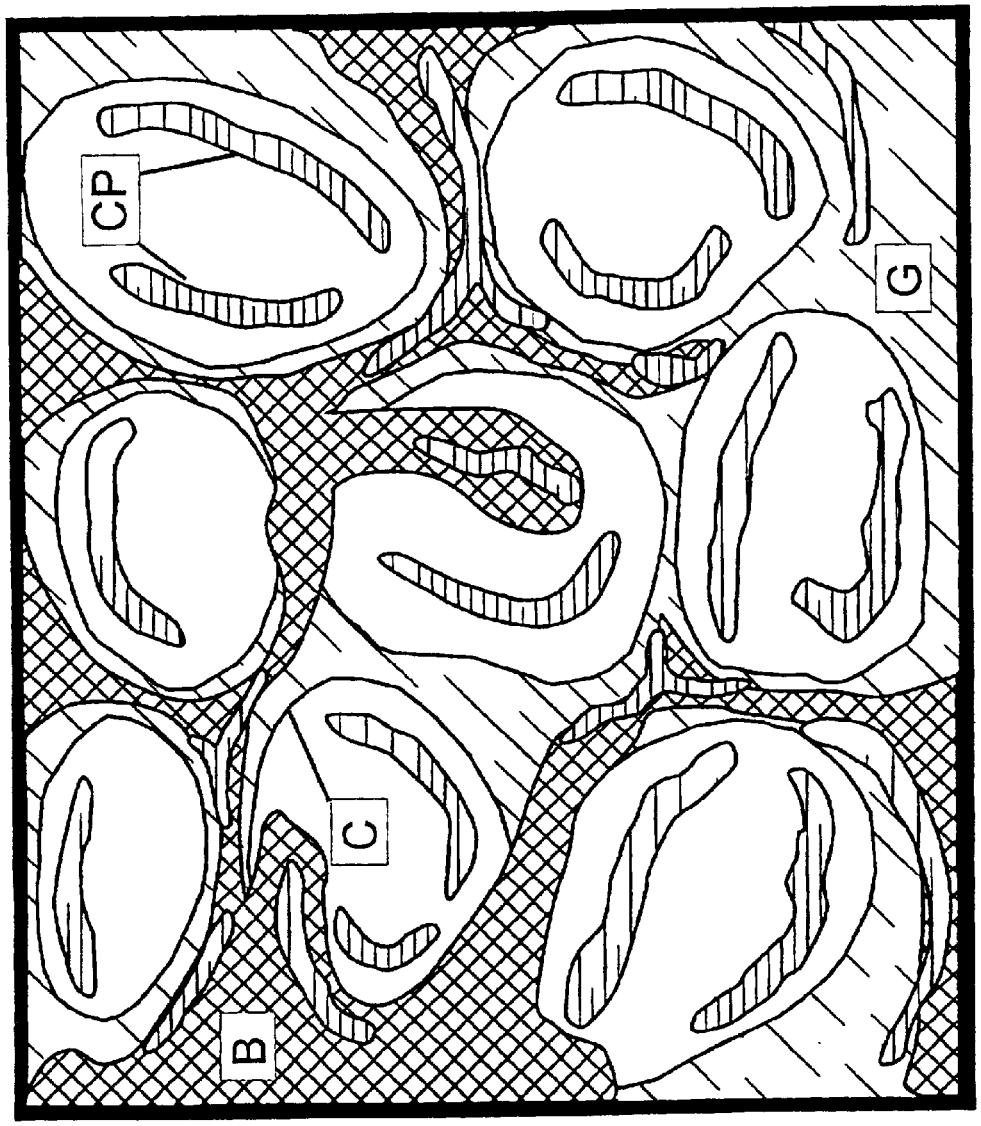
FIG. 3 is a view sequential to that of FIG. 2 showing the beginning of resorption of the polymer containing particles of the implant composition.

FIG. 3 shows the second phase of the resorption, i,e., resorption of the polymer containing particles. This occurs as early as four weeks or as late as twenty weeks after applying the implant composition, depending upon the particular formulation of the composition and application. In the example, as reflected in FIG. 3, the polymer coating has partially broken down allowing resorption of the encapsulated calcium sulfate compound. Therein, the resorbing calcium sulfate compound produces deposits of calcium phosphate (CP) as in the first phase of resorption (see FIG. 2), and additional bone ingrowth will occur.

Figure 4:
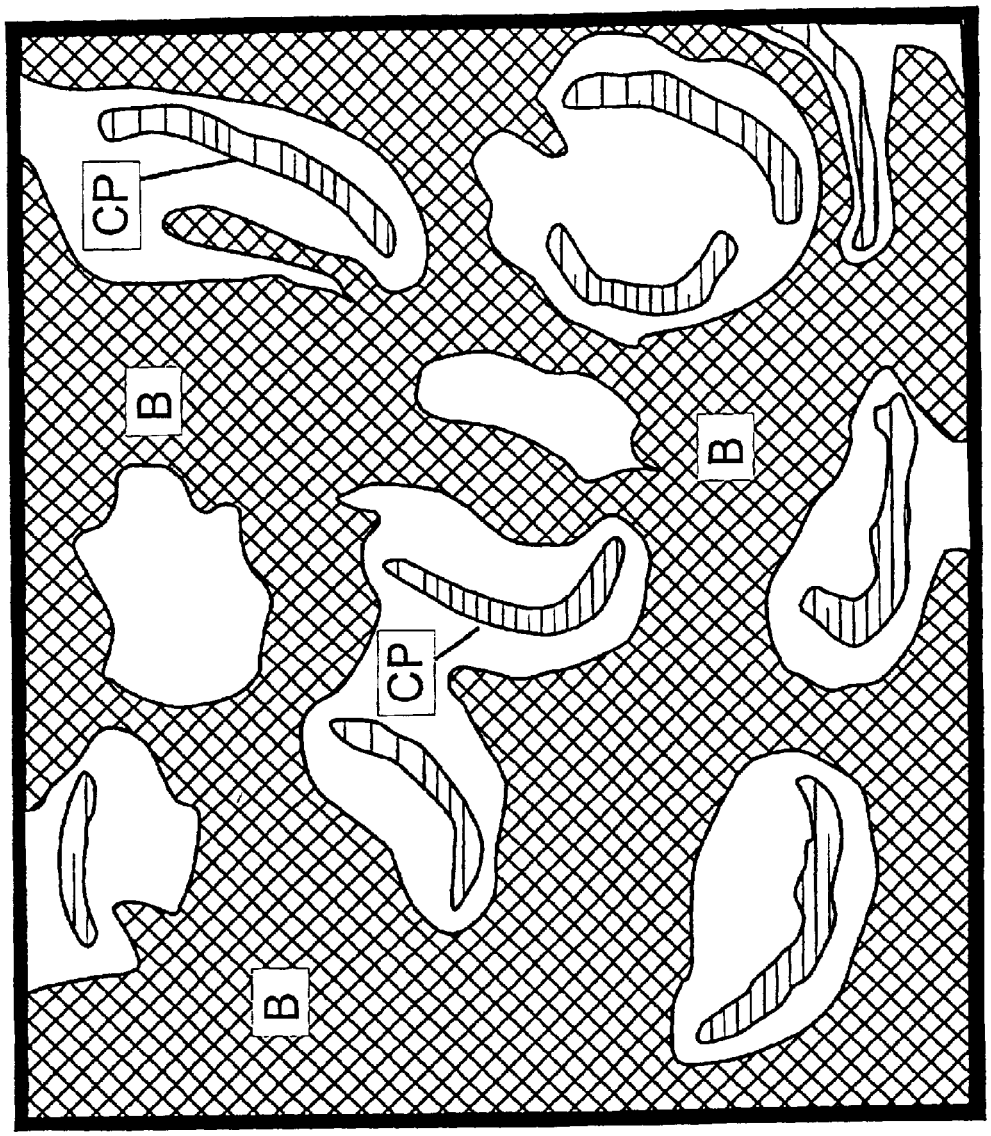
FIG. 4 is a view, sequential to that of FIG. 3, showing the end result of the bioresorption of the implant composition, which results stimulated bone growth with diminishing level of the implant composition.

FIG. 4 shows the end result of the resorption of the implant composition. This occurs as early as six weeks or as late as twenty four weeks depending upon the particular formulation of the composition and application. By this time only residual amount of polymer material remains and full bone ingrowth has occurred. In addition, most calcium phosphate deposits have been removed by bone remodeling, only a small amount of calcium phosphate deposits within the original particles can still be visible in new bone growth. It is understood that bone remodeling is a natural process that normally occurs very slowly. Remodeling occurs as new bone is constantly formed by osteoblasts and removed by osteoclasts. The balance of the two processes represents an equilibrium that determines how much bone is present at any given time. However, remodeling is rapid during healing, and virtually all of the immature bone that is formed during early healing is remodeled and replaced by more mature bone. The calcium phosphate deposits formed by the dissolving calcium sulfate are similar to bone mineral, and are also remodeled and replaced by more mature bone during this period of time.

The implant composition of the present invention can be used for the repair, augmentation, and other treatment of bone. The implant composition possesses significant advantages over existing calcium sulfate cements and pellets used clinically for bone repair and regeneration. More particularly, current calcium sulfate materials are resorbed by human bone within two to seven weeks, depending upon the calcium sulfate form and the particular surgical site, however, cannot be retained at the site for longer periods. As noted, such material is resorbed faster than it can be replaced by new bone thereby reducing its value to both patient and practitioner. The implant composition of the present invention can be designed to resorb in phases in accordance with the needs of a specific surgical application and environment of a recipient site, therein allowing substantial control of resorption rate. The resorption rate can be controlled of between eight and twenty four weeks, which substantially matches the rate of bone growth.

On the other hands, since methods involving separate use of calcium sulfate and polymeric components have long been established as safe and fully bioresorbable, clinical utilities and feasibility of the present invention are apparent.

In particular, the implant composition of the present invention can be applied in dentistry for bone repairing and augmentation with or without a surgical implant.

Figure 5:
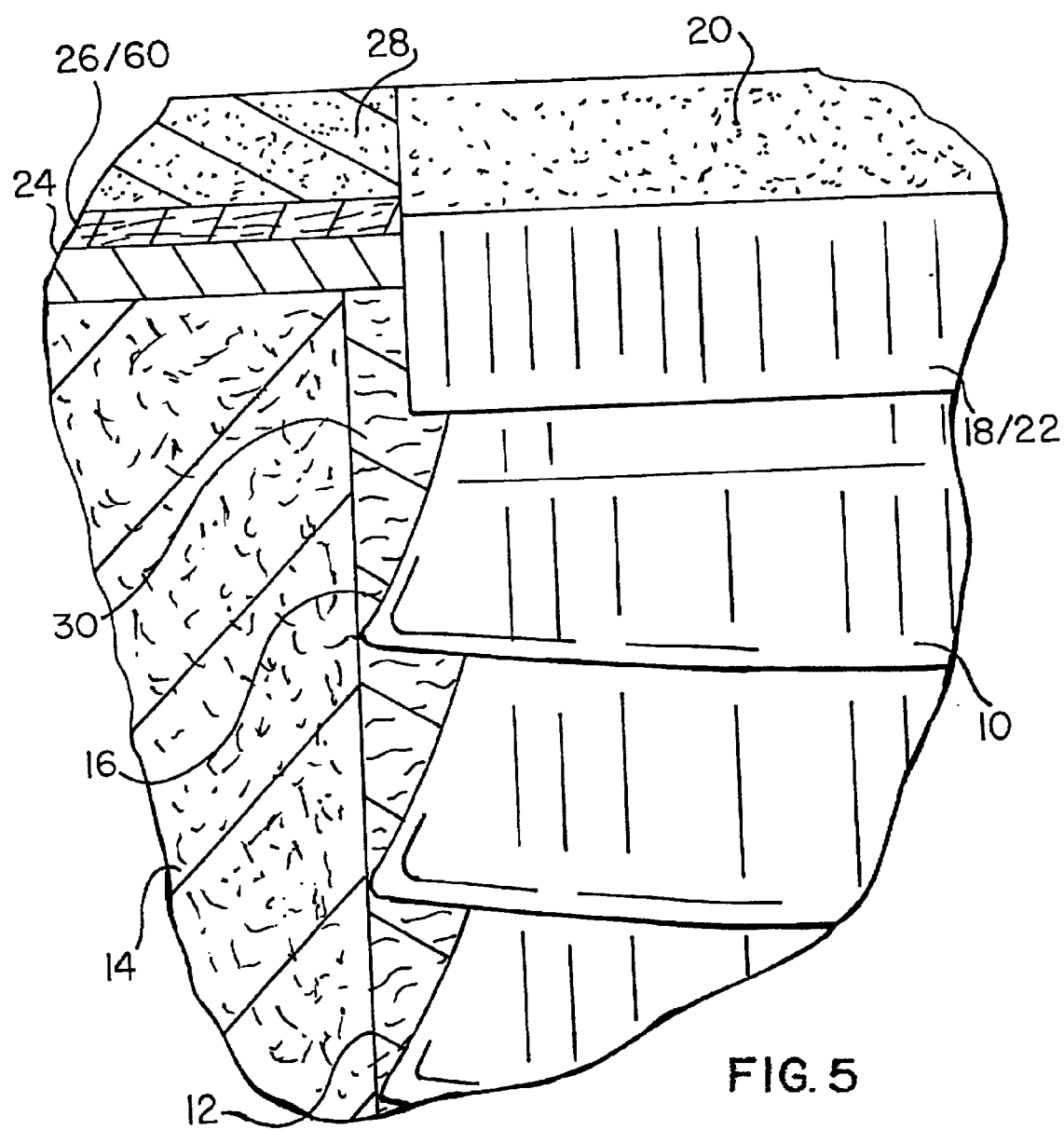
FIG. 5 is a cross-sectional schematic view of the implant composition of the present invention used with a surgical implant which has buttress threads.
Figure 7:
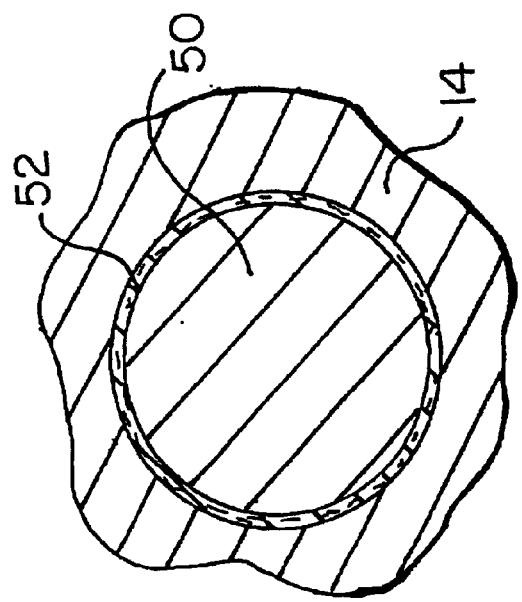
FIGS. 6 and 7 show a cross-sectional schematic view and a top view, respectively, of the implant composition of the present invention used with a surgical implant which has a smooth exterior surface.
Figure 6:
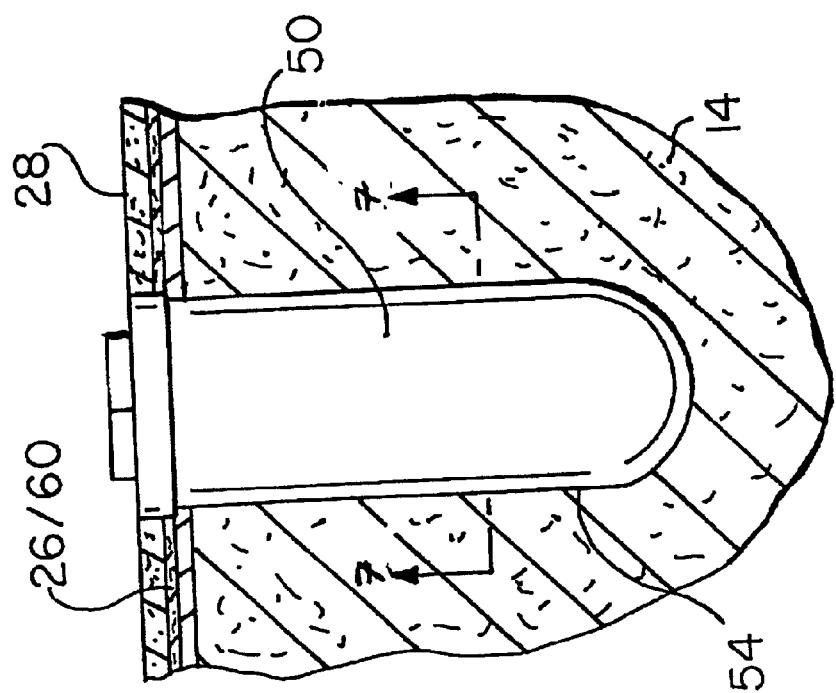

FIG. 5 shows an example of using the implant composition of the present invention with a surgical implant. As shown, a surgical implant 10 is furnished at a surgical site 12 for the purpose of establishing bio-integration with surrounding bone tissue 14. An implant of the type of implant 10 includes buttress treads 16 (or other threading) and an integral collar 18 which comprises an upper part 20 and a lower part 22. Located above bone tissue 14 is a cortical bone layer 24, an optional bio-resorbable barrier layer 26 (described below) and a gum or soft tissue layer 28. The implant composition 30 of the present invention is filled in between bone tissue 14 and surgical implant 10 as an osseo-stimulative. It is to be understood that the implant composition can be applied to implant 10 before insertion into the osseotomy site or can be applied to the site 12, prior to insertion of the implant. Further, any of the surfaces of implant 10 inclusive of parts 20 and 22 of the collar 18 can be provided with cell growth stimulative microgeometry in accordance with our co-pending Application Ser. No. 09/500,038. When a surgical implant exhibits an entirely smooth external geometry, as is the case with an implant 50 in FIG. 6, an osseo-stimulative surface 52 (FIG. 7) made of the implant composition of the present invention is more suitable when physically adhered to the implant at a pre-operative site. It is, however, to be appreciated that a paste of the implant composition can be applied to an osseotomy site in combination with use of implant 50 and its osseo-stimulative surface 52.

The implant materials of the present invention can be sold as a kit. The kit can comprise dry powder of calcium sulfate compound, one or more types of polymer containing particles. The kit can further comprise a setting agent packed in a container. The kit can also include instructions on how to prepare the implant mixture, apply it in a recipient site and set it into the solid implant composition.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth herewith.

We claim:

1. An implant composition for stimulating bone growth, comprising:
   (a) a first calcium sulfate compound,
   (b) polymer containing particles comprising a second calcium sulfate compound, and at least one resorbable polymer, and
   (c) a setting agent for setting said calcium sulfate compound and said polymer containing particles into a heterogeneous solid composition,
   wherein upon setting, said calcium sulfate compound forms a matrix and said polymer containing particles are settled within said matrix.

2. The implant composition of claim 1, wherein a rate of resorption of said implant composition in a recipient site is in a range from about four weeks to about twenty eight weeks.

3. The implant composition of claim 1, wherein said matrix and said polymer containing particles resorb at different rates in a recipient site, and resorption of said polymer containing particles being slower.

4. The implant composition of claim 1, wherein said first calcium sulfate compound is calcium sulfate hemihydrate.

5. The implant composition of claim 1, wherein said setting agent is selected from the group consisting of water, an alkaline metal salt solution, and a potassium salt solution.

6. The implant composition of claim 1, wherein size of said polymer containing particles is more than 20 μm in diameter.

7. The implant composition of claim 1, wherein said second calcium sulfate compound in said polymer containing particles is selected from the group consisting of calcium sulfate dihydrate, calcium sulfate hemihydrate, and mixture thereof.

8. The implant composition of claim 1, wherein said resorbable polymer is mixed with said calcium sulfate compound of said particles.

9. The implant composition of claim 1, wherein said calcium sulfate compound of said particles is coated with a resorbable polymer coating.

10. The implant composition of claim 9, wherein thickness of said resorbable polymer coating is from about 2 μm to about 50 μm.

11. The implant composition of claim 1, wherein said resorbable polymer is aliphatic polyesters of alpha-hydroxy acid derivatives.

12. The implant composition of claim 11, wherein said resorbable polymer is selected from the group consisting of polyactides, polyglycolides, polydioxanone, and poly ε-caprolactone.

13. The implant composition of claim 11, wherein said resorbable polymer is polyactides.

14. The implant composition of claim 1, wherein said resorbable polymer is a poly(desaminotyrosyl-tyrosine ethyl ester carbonate).

15. The implant composition of claim 1, wherein said resorbable polymer is selected from the group consisting of hydrophobic polymers, carnuba waxes, water soluble polymers, polyvinyl alcohols, and therapeutic polymers containing salicylates.

16. The implant composition of claim 1, wherein the amount of said resorbable polymer in said polymer containing particle is in a range from about 0.1% to about 50% (w/w).

17. A kit of implant materials for bone augmentation and bone defect reparation comprising:
  (a) dry powder of a first calcium sulfate compound, and
  (b) polymer containing particles comprising a second calcium sulfate compound, and at least one resorbable polymer.

18. The kit of implant materials of claim 17, wherein said first calcium sulfate compound is calcium sulfate hemihydrate.

19. The kit of implant materials of claim 17, wherein size of said polymer containing particles is more than 20 μm in diameter.

20. The kit of implant materials of claim 17, wherein said second calcium sulfate compound in said polymer containing particles is selected from the group consisting of calcium sulfate dihydrate, calcium sulfate hemihydrate, and mixture thereof.

21. The kit of implant materials of claim 17, wherein said resorbable polymer is mixed with said calcium sulfate compound of said particles.

22. The kit of implant materials of claim 17, wherein said calcium sulfate compound of said particles is coated with a resorbable polymer coating.

23. The kit of implant materials of claim 22, wherein thickness of said resorbable polymer coating is from about 2 μm to about 50 μm.

24. The kit of implant materials of claim 17, wherein said resorbable polymer is aliphatic polyesters of alpha-hydroxy acid derivatives.

25. The kit of implant materials of claim 24, wherein said resorbable polymer is selected from the group consisting of polyactides, polyglycolides, polydioxanone, and poly ε-caprolactone.

26. The kit of implant materials of claim 24, wherein said resorbable polymer is polyactides.

27. The kit of implant materials of claim 17, wherein said resorbable polymer is a poly(desaminotyrosyl-tyrosine ethyl ester carbonate).

28. The kit of implant materials of claim 17, wherein said resorbable polymer is selected from the group consisting of hydrophobic polymers, carnuba waxes, water soluble polymers, polyvinyl alcohols, and therapeutic polymers containing salicylates.

29. The kit of implant materials of claim 17, wherein the amount of said resorbable polymer in said polymer containing particle is in a range from about 0.1% to about 30% (w/w).

30. The kit of implant materials of claim 17, wherein said kit comprises two different polymer containing particles that resorb at different rates in a recipient site.

31. The kit of implant materials of claim 17 further comprising a setting agent, packed in a container.

32. The kit of implant materials of claim 31, wherein said setting agent is selected from the group consisting of water, an alkaline metal salt solution, and a potassium salt solution.

33. The kit of implant materials of claim 17 further comprising instructions on how to use the kit.

34. A method for bone augmentation and bone defect reparation comprising the steps of:
  (a) mixing a calcium sulfate compound and resorbable polymer coated particles with a setting agent into a mixture,
  (b) applying said mixture, and
  (c) setting said mixture into a heterogeneous solid composition, wherein upon setting, said calcium sulfate compound forms a matrix and said resorbable polymer coated particles settled within said matrix;
  wherein said heterogeneous solid composition resorbs at a controlled rate in a recipient site for stimulating bone growth.

35. The method of claim 34, wherein applying said mixture is filling a recipient site with said mixture.

36. The method of claim 34, wherein applying said mixture is coating said mixture on a surface of a surgical implant prior to introducing said surgical implant into said recipient site.

37. The method of claim 34, wherein said setting agent controls a speed of setting said mixture into a heterogeneous solid composition.

38. The method of claim 37, wherein said setting agent is selected from the group consisting of water, an alkaline metal salt solution, and a potassium salt solution.

39. The method of claim 34, wherein said resorbable polymer coated particles resorbable polymer coated particles that resorb at different rates in a recipient site.

40. An implant composition for stimulating bone growth, comprising:
  (a) a calcium sulfate compound,
  (b) resorbable polymer coated particles, and
  (c) a setting agent for setting said calcium sulfate compound and said resorbable polymer coated particles into a heterogeneous solid composition, wherein upon setting, said calcium sulfate compound forms a matrix and said resorbable polymer coated particles are settled within said matrix.

41. The implant composition of claim 40, wherein said matrix and said resorbable polymer coated particles resorb at different rates in a recipient site, and resorption of said resorbable polymer coated particles being slower.

42. The implant composition of claim 41, wherein a rate of resorption of said implant composition in a recipient site is in a range from about four weeks to about twenty eight weeks.

43. The implant composition of claim 41, wherein said calcium sulfate compound is calcium sulfate hemihydrate.

44. The implant composition of claim 41, wherein said setting agent is selected from the group consisting of water, an alkaline metal salt solution, and a potassium salt solution.

45. The implant composition of claim 41, wherein said resorbable polymer coated particles comprise:
  (a) a calcium sulfate compound, and
  (b) a polymer coating with at least one resorbable polymer.

46. The implant composition of claim 45, wherein size of said resorbable polymer coated particles is more than 20 $\mu$m in diameter.

47. The implant composition of claim 45, wherein said calcium sulfate compound in said resorbable polymer coated particles is selected from the group consisting of calcium sulfate dihydrate, calcium sulfate hemihydrate, and mixture thereof.

48. The implant composition of claim 47, wherein thickness of said polymer coating is from about 2 $\mu$m to about 50 $\mu$m.

49. The implant composition of claim 48, wherein said resorbable polymer is aliphatic polyesters of alpha-hydroxy acid derivatives.

50. The implant composition of claim 49, wherein said resorbable polymer is selected from the group consisting of polyactides, polyglycolides, polydioxanone, and poly $\epsilon$-caprolactone.

51. The implant composition of claim 49, wherein said resorbable polymer is polyactides.

52. The implant composition of claim 48, wherein said resorbable polymer is a poly(desaminotyrosyl-tyrosine ethyl ester carbonate).

53. The implant composition of claim 48, wherein said resorbable polymer is selected from the group consisting of hydrophobic polymers, carnuba waxes, water soluble polymers, polyvinyl alcohols, and therapeutic polymers containing salicylates.

54. The implant composition of claim 48, wherein the amount of said resorbable polymer in said resorbable polymer coated particles is in a range from about 0.1% to about 50% (w/w).

55. A kit of implant materials for bone augmentation and bone defect reparation comprising:
  (a) dry powder of a calcium sulfate compound, and
  (b) resorbable polymer coated particles.

56. The kit of implant materials of claim 55, wherein said calcium sulfate compound is calcium sulfate hemihydrate.

57. The kit of implant materials of claim 55, wherein said resorbable polymer coated particles comprise:
  (a) a calcium sulfate compound, and
  (b) a polymer coating with at least one resorbable polymer.

58. The kit of implant materials of claim 57, wherein size of said resorbable polymer coated particles is more than 20 $\mu$m in diameter.

59. The kit of implant materials of claim 57, wherein said calcium sulfate compound in said resorbable polymer coated particles is selected from the group consisting of calcium sulfate dihydrate, calcium sulfate hemihydrate, and mixture thereof.

60. The kit of implant materials of claim 59, wherein thickness of said polymer coating is from about 2 $\mu$m to about 50 $\mu$m.

61. The kit of implant materials of claim 60, wherein said resorbable polymer is aliphatic polyesters of alpha-hydroxy acid derivatives.

62. The kit of implant materials of claim 61, wherein said resorbable polymer is one selected from the group consisting of polyactides, polyglycolides, polydioxanone, and poly $\epsilon$-caprolactone.

63. The kit of implant materials of claim 61, wherein said resorbable polymer is polyactides.

64. The kit of implant materials of claim 60, wherein said resorbable polymer is a poly(desaminotyrosyl-tyrosine ethyl ester carbonate).

65. The kit of implant materials of claim 60, wherein said resorbable polymer is selected from the group consisting of hydrophobic polymers, carnuba waxes, water soluble polymers, polyvinyl alcohols, and therapeutic polymers containing salicylates.

66. The kit of implant materials of claim 60, wherein the amount of said resorbable polymer in said resorbable polymer coated particles is in a range from about 0.1% to about 30% (w/w).

67. The kit of implant materials of claim 57, wherein said kit comprises two different resorbable polymer coated particles that resorb at different rates in a recipient site.

68. The kit of implant materials of claim 57, further comprising a setting agent, packed in a container.

69. The kit of implant materials of claim 68, wherein said setting agent is selected from the group consisting of water, an alkaline metal salt solution, and a potassium salt solution.

* * * * *

UNITED STATES PATENT AND TRADEMARK OFFICE
CERTIFICATE OF CORRECTION

PATENT NO. : 6,770,695 B2
DATED : August 3, 2004
INVENTOR(S) : John L. Ricci, Harold Alexander and Bruce Hollander It is certified that error appears in the above-identified patent and that said Letters Patent is hereby corrected as shown below:

Column 4,
Lines 15, 26 and 27, change "polyactides" to -- polylactides --.

Column 7,
Lines 27 and 30, change "polyactides" to -- polylactides --.

Column 8,
Lines 6 and 9, change "polyactides" to -- polylactides --.

Column 9,
Lines 38 and 41, change "polyactides" to -- polylactides --.

Column 10,
Lines 28 and 31, change "polyactides" to -- polylactides --.

Signed and Sealed this

Twenty-first Day of February, 2006

JON W. DUDAS
*Director of the United States Patent and Trademark Office*